United States Patent [19]
Lynn

[11] Patent Number: 5,358,495
[45] Date of Patent: Oct. 25, 1994

[54] STERILE GUIDEWIRE EXCHANGE SYSTEM

[76] Inventor: Lawrence A. Lynn, 862 Curleys Ct., Worthington, Ohio 43235

[21] Appl. No.: 11,696

[22] Filed: Feb. 1, 1993

[51] Int. Cl.$^5$ ............................................. A61M 5/00
[52] U.S. Cl. ................................. 604/171; 604/263; 604/163; 604/53
[58] Field of Search .................. 604/52, 53, 163, 164, 604/171, 172, 280, 283, 263

[56] References Cited

U.S. PATENT DOCUMENTS

| | | | |
|---|---|---|---|
| 3,095,972 | 7/1963 | Sorenson | 604/163 |
| 3,825,001 | 7/1974 | Bennet et al. | 604/171 |
| 4,326,520 | 4/1982 | Alley | 604/171 |
| 4,772,275 | 9/1988 | Erlich . | |
| 4,834,710 | 5/1989 | Fleck | 604/163 |
| 4,850,974 | 7/1989 | Bickelhaupt | 604/171 |
| 4,925,448 | 5/1990 | Bazaral | 604/171 |
| 4,943,284 | 7/1990 | Erlich . | |
| 5,061,246 | 10/1991 | Anapliotis | 604/171 |
| 5,125,906 | 6/1992 | Fleck . | |
| 5,181,913 | 1/1993 | Erlich . | |
| 5,234,411 | 8/1993 | Vaillancourt | 604/171 |
| 5,263,938 | 11/1993 | Orr . | |

*Primary Examiner*—John G. Weiss
*Attorney, Agent, or Firm*—Cushman, Darby & Cushman

[57] ABSTRACT

An enclosed guidewire exchange system is described which utilizes a flexible sterile barrier which is preferably tubular and folded or rolled prior to use. The barrier functions to enclose the old catheter as it is being withdrawn from the patient. The system also provides a sterile barrier for enclosure of the guidewire upon removal of the old catheter from over the guidewire. Thus, the system preferably includes a guidewire container containing a flexible guidewire. The container includes a connector which may be a threaded female end for attachment to the pilot tube luer of the distal port of the multilumen catheter or other indwelling catheter. The guidewire container preferably includes an interrupted portion such as a window to allow the physician to contact the guidewire within the container so as to advance the guidewire into catheter once the container has been connected to the luer of the catheter. The sterile barrier enclosure is preferably attached to the guidewire container proximal to the female connector and unfolds or unrolls to provide a sterile cavity distal to the guidewire container. The sterile barrier can include a proximal catheter barrier portion and a distal guidewire barrier portion and a tear point or region intermediate those portions. The system may further include a sterile catheter for placement over the guidewire.

28 Claims, 7 Drawing Sheets

STERILE GUIDEWIRE EXCHANGE SYSTEM

BACKGROUND OF THE INVENTION

Intravascular catheters commonly become colonized with bacteria and/or fungi during the indwelling period. The longer a catheter is allowed to remain in place the greater the probability of colonization and secondary infection of the patient. This is particularly common with multilumen catheters entering either the subclavian or internal jugular veins. Since the probability of colonization is a function of the indwelling time, these catheters are commonly exchanged with a new sterile catheter through the same site over a guidewire. Present techniques for guidewire exchange, however, are cumbersome and are difficult to perform while maintaining sterility.

The technique for guidewire exchange involves the preparation of the old catheter site at the point of entrance of the catheter into the patient. Using the fingers and commonly utilizing a stiff guide covering the distal portion of a J-tipped catheter, the guidewire is inserted from a guidewire container through the distal port of a multilumen catheter until the guidewire extends well into the catheter. The catheter is then withdrawn over the guidewire. Subsequent to this, a new sterile catheter is inserted over the guidewire in the old catheter's place. The guidewire is then removed and the catheter is attached to a fluid system.

Unfortunately, it is common for the old catheter to contaminate the physician's gloves during the procedure and, therefore, contaminate the new catheter by transfer of these bacteria during the insertion process (conventional multilumen catheters are generally 20–30 cm in length). A variety of techniques utilizing multiple drapes and multiple sets of sterile gloves are well known in the art. These techniques remain cumbersome and unreliable. It is particularly difficult to maintain a sterile field for the guidewire which remains within the insertion site at the time the old catheter is removed. This guidewire is flexible and a large portion of this guidewire must remain out of the patient to avoid excessive penetration into the patient which could result in cardiac or vascular injury. It is very difficult for the physician to maintain the sterility of this flexible guidewire within a sterile field which is commonly contaminated by the old catheter which has been removed and may have contacted the surrounding environment in juxtaposition with the guidewire. In fact, a recent study has shown that guidewire exchange may not be associated with a reduction in infection-related complications. This failure to reduce infection may be due to the fact that many of the sterile catheters which are exchanged over guidewires are contaminated during the exchange process.

For these reasons, there has long been a critical need to provide an inexpensive over-the guidewire catheter exchange system which eliminates the potential for contamination of the new catheter during catheter exchange.

SUMMARY OF THE INVENTION

The present invention comprises an enclosed guidewire exchange system and method which utilized a flexible sterile barrier which is preferably tubular and folded or rolled prior to use. The barrier functions to enclose the old catheter as it is being withdrawn from the patient, the system further providing a sterile barrier for enclosure of the guidewire upon removal of the old catheter from over the guidewire.

The system preferably includes a guidewire container containing a flexible guidewire. The container includes a connector which may be a threaded female end for attachment to the pilot tube luer of the distal port of the multilumen catheter or other indwelling catheter. The guidewire container preferably includes an interrupted portion such as a window to allow the physician to contact the guidewire within the container so as to advance the guidewire into the catheter once the container has been connected to the luer of the catheter. The sterile barrier enclosure is provided, which is preferably attached to the guidewire container proximal to the female connector and unfolds or unrolls to provide a sterile cavity distal to the guidewire container. The sterile barrier can include a proximal catheter barrier portion and a distal guidewire barrier portion and a tear point or region intermediate the portions. The system further includes a sterile catheter for replacement over the guidewire.

In operation, the site surrounding the entry of the catheter into the skin is sterilely prepped. The connector of the guidewire container is then attached to the luer of the distal port of the catheter. The physician then puts on sterile gloves and grasps the guidewire through the guidewire container windows and advances the guidewire to a predetermined point. The sterile barrier is then unfolded or unrolled and advanced partly over the old catheter. Once the proximal portion of the old catheter is enclosed, the old catheter is then retracted completely into the sterile barrier until a small portion of the guidewire extends beyond the distal tip of the catheter into the insertion site. At this point, the catheter barrier is fully extended to the tip of the old catheter. The physician then advances as by unrolling or unfolding the guidewire barrier slightly over the guidewire. The physician then grasps the distal portion of the guidewire barrier against the guidewire to prevent further retraction of the guidewire out of the patient. With the other hand, the physician grasps the old catheter through the catheter barrier and pulls the old catheter off the guidewire. As this maneuver is accomplished, the guidewire barrier expands from its previously compressed position to entirely cover that portion of the guidewire extending outside the patient from which the old catheter has now been removed. The physician now has a sterile guidewire extending from the patient which is completely covered by the guidewire barrier portion which is continuous with the catheter barrier portion which contains the old catheter. The physician grasps the distal portion of the catheter barrier in one hand and the proximal portion of the guidewire barrier in the other hand and separates the two barriers, thereby removing the catheter barrier with its contained contaminated catheter from the guidewire barrier. The physician then grasps the proximal portion of the guidewire through the guidewire barrier and slides the guidewire barrier downward toward the patient to exposure approximately 1 cm of the end of the guidewire. With the other hand, the physician grasps the new multilumen catheter and inserts the tip over the guidewire and advances the catheter through the guidewire barrier, over the guidewire, and into the patient to the proper position. The guidewire barrier is then removed from around the multilumen catheter and the catheter is sutured in place. With this system, the entire process can be accomplished without the risk of contact contamination of either the guidewire or the new catheter.

It is the purpose of this invention to provide an over-the-guidewire catheter exchange system which reduces the risk of contact contamination of either the guidewire or the catheter during the insertion process. It is further the purpose of this invention to provide a simplified method of sterile catheter exchange. Additional objects and advantages of the invention will be set forth in the description which follows, and in part will be evident from the description, or may be learned by practice of the invention. The objects and advantages of the invention may be realized by means of the instrumentalities and combinations particularly pointed out in the appended claims.

DESCRIPTION OF THE PREFERRED EMBODIMENT

Figure 1:
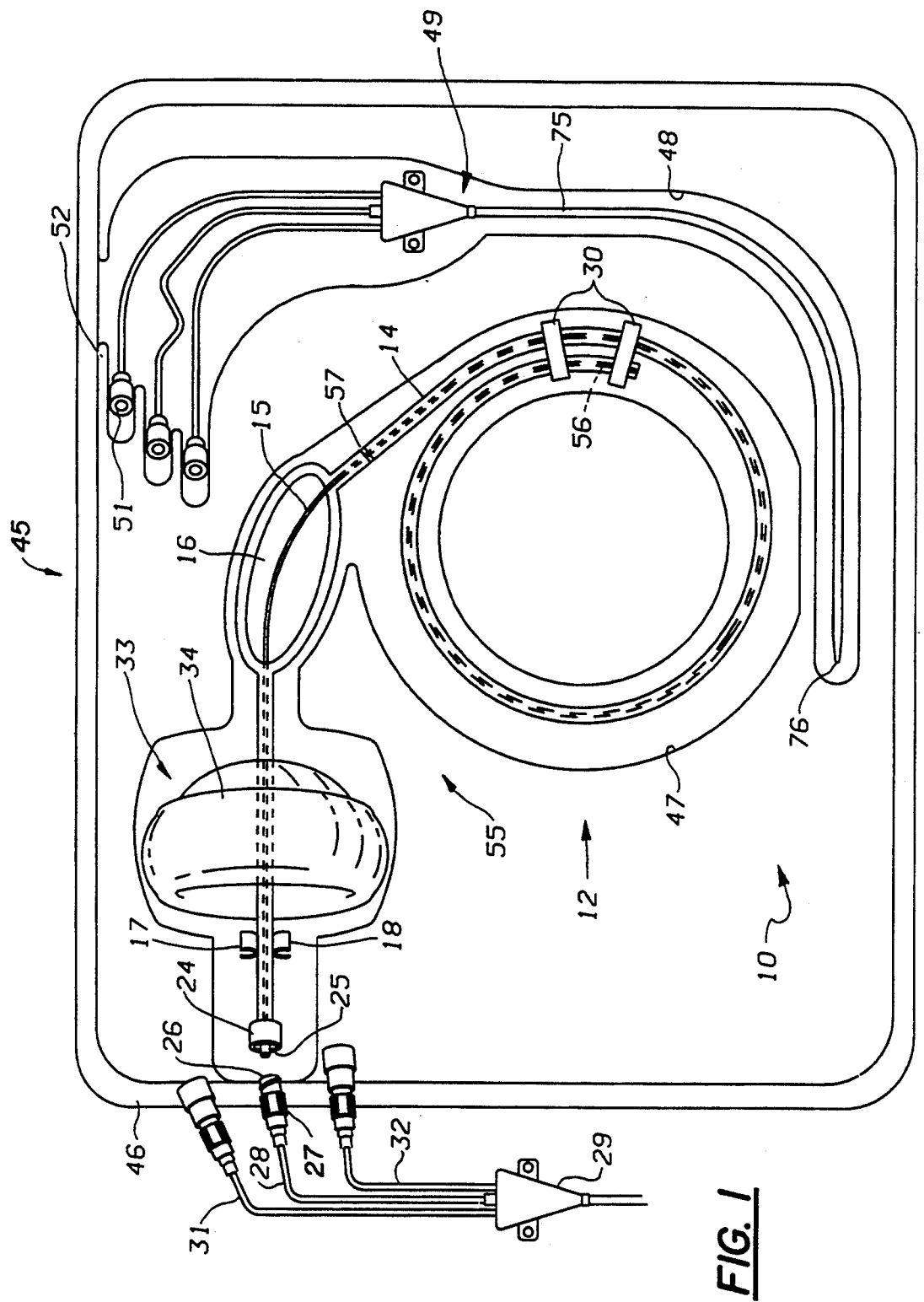
FIG. 1 is a top view of the system showing the assembly within a vacuformed package and the exchange barrier in a rolled position.

FIG. 1 shows generally a over-the-guidewire sterile catheter exchange system 10 including exchange assembly 12, having a guidewire container 14 containing J-tipped guidewire 15. The guidewire container 14 includes finger contact windows 16. The guidewire container 14 has clips 17 and 18. The guidewire container 14 further has a female threaded connector 24 at its distal end 25 for connection to the male luer 26 of the distal port 27 of pilot tube 28 of a conventional central venous catheter 29. The guidewire container is held together by fasteners 30. Catheter 29 is shown with additional proximal tube 31 and middle tube 32. An exchange barrier 33 is provided (shown rolled in FIG. 1). The exchange barrier 33 has a proximal old catheter barrier portion 34 and the more distal guidewire barrier portion 36 (shown unrolled in FIG. 2). The two barrier portions are connected along a weakened portion 38, the two barrier portions can be disengaged at the weakened area 38 as will be discussed below. The exchange barrier 33 is connected, as by adhesive, near its proximal end 42 about the guidewire container 14 at barrier connection site 44. Prior to operation, the catheter barrier 34 is rolled into a relatively tight roll (FIG. 1) in juxtaposition with its connection 44 with the guidewire container 14. The catheter barrier 34 is preferably longer than the catheter 29 and is preferably greater than 20 cm in length. In this position, before use, the distal guidewire barrier portion 36 (shown unrolled in FIG. 2) is folded and rolled within the outer rolled catheter barrier portion 34. The guidewire barrier 36 is preferably greater than 20 cm in length.

The entire assembly 12 is preferably provided within a vacuformed sterile package 45 having a conventional lid (not shown) attached as by adhesive along rim 46. A guidewire container recess 47 and a catheter recess 48 are included. A sterile catheter 49 is included within the catheter recess 48. The catheter injection caps are held in an upright position by vacuformed cap holders 52 to allow one handed injections through the caps 51 for flushing catheter 29. The distance separating the capholders is slightly less than the diameter of the caps, thereby tightly holding the caps in a vertical position.

Figure 2:
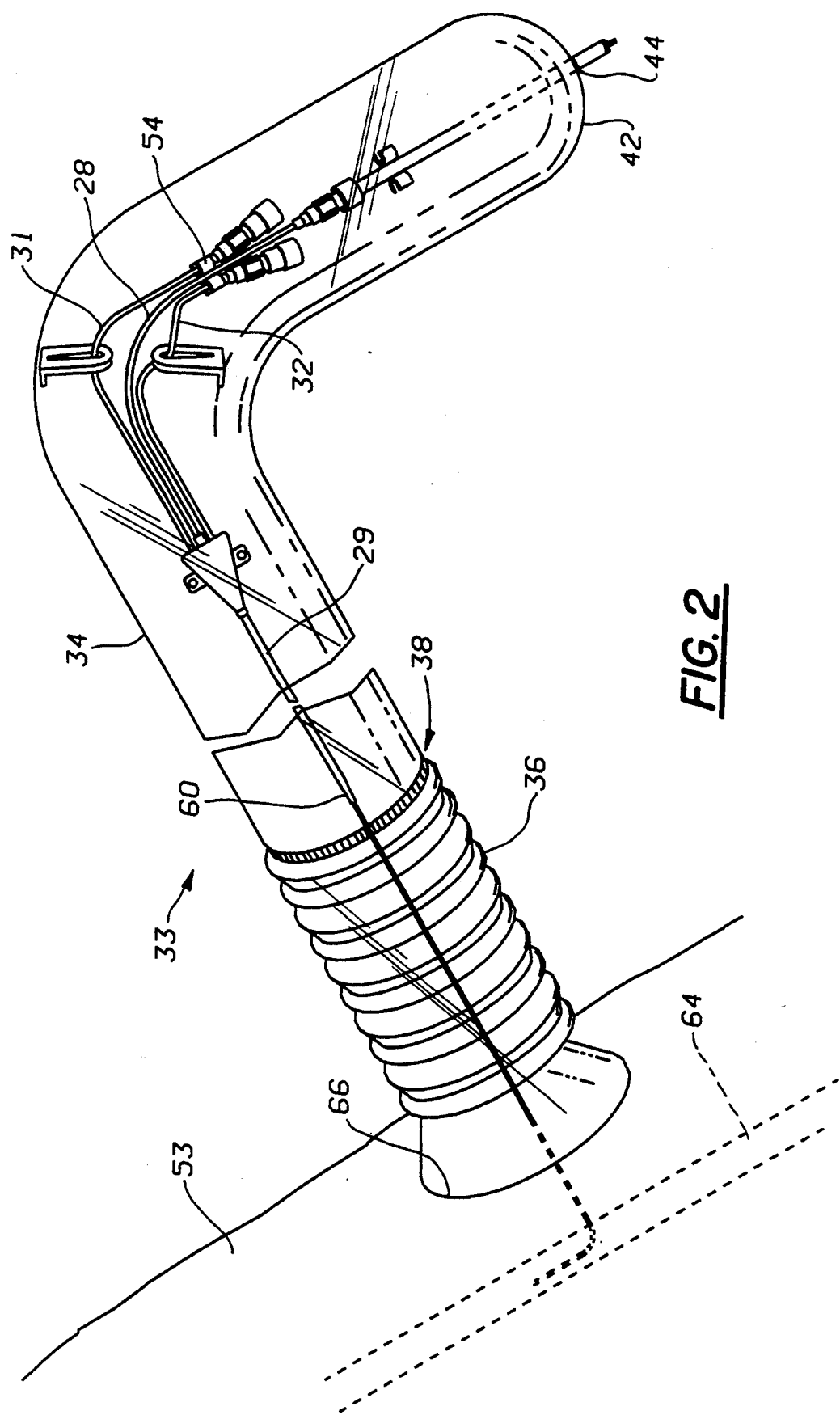
FIG. 2 illustrates the operation of the assembly, showing the exchange barrier extended over the catheter with the barrier against the patient's skin and the guidewire extending into the patient's blood vessel.
Figure 3:
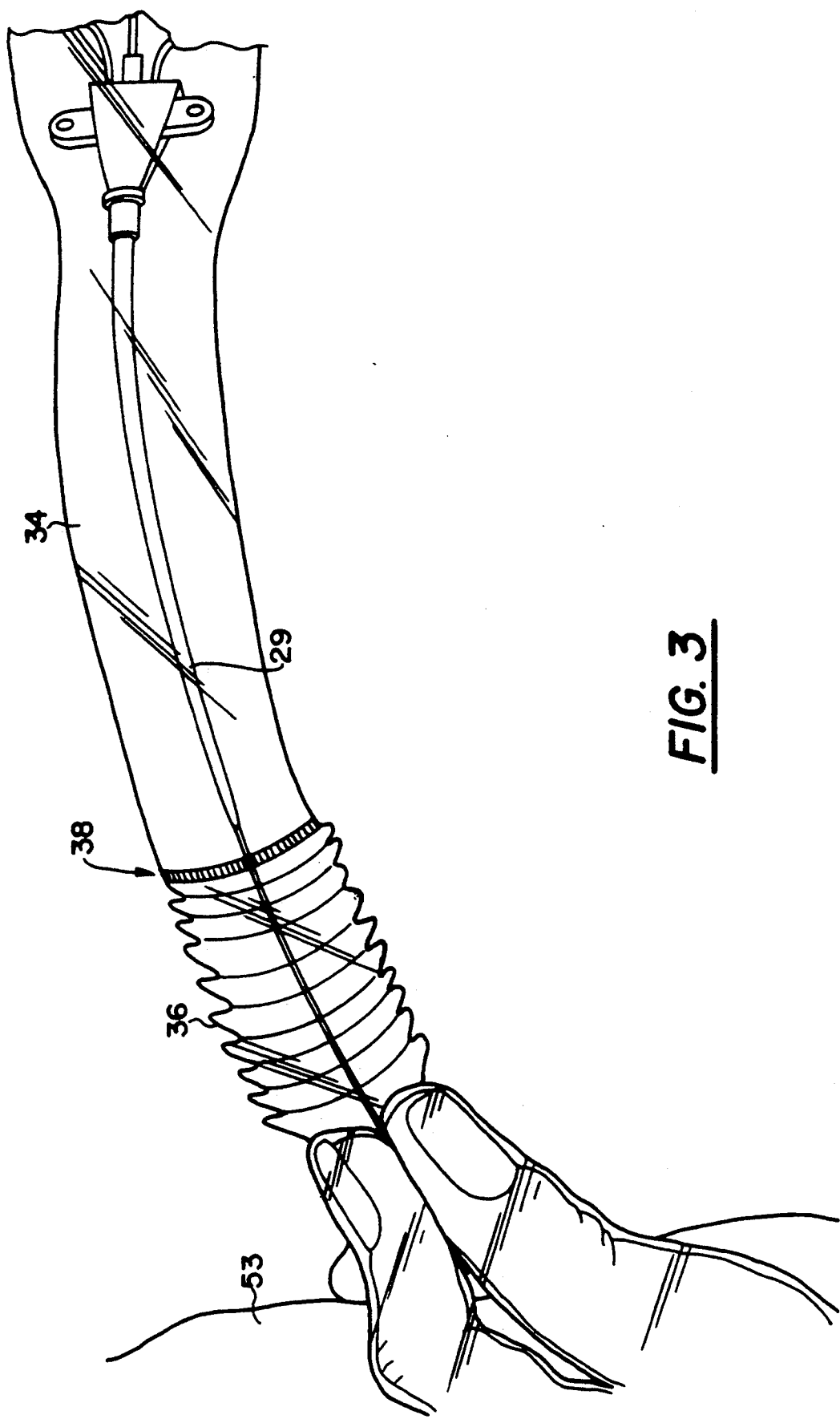
FIG. 3 illustrates the operation of the assembly, showing the guidewire being grasped through the guidewire barrier.
Figure 4:
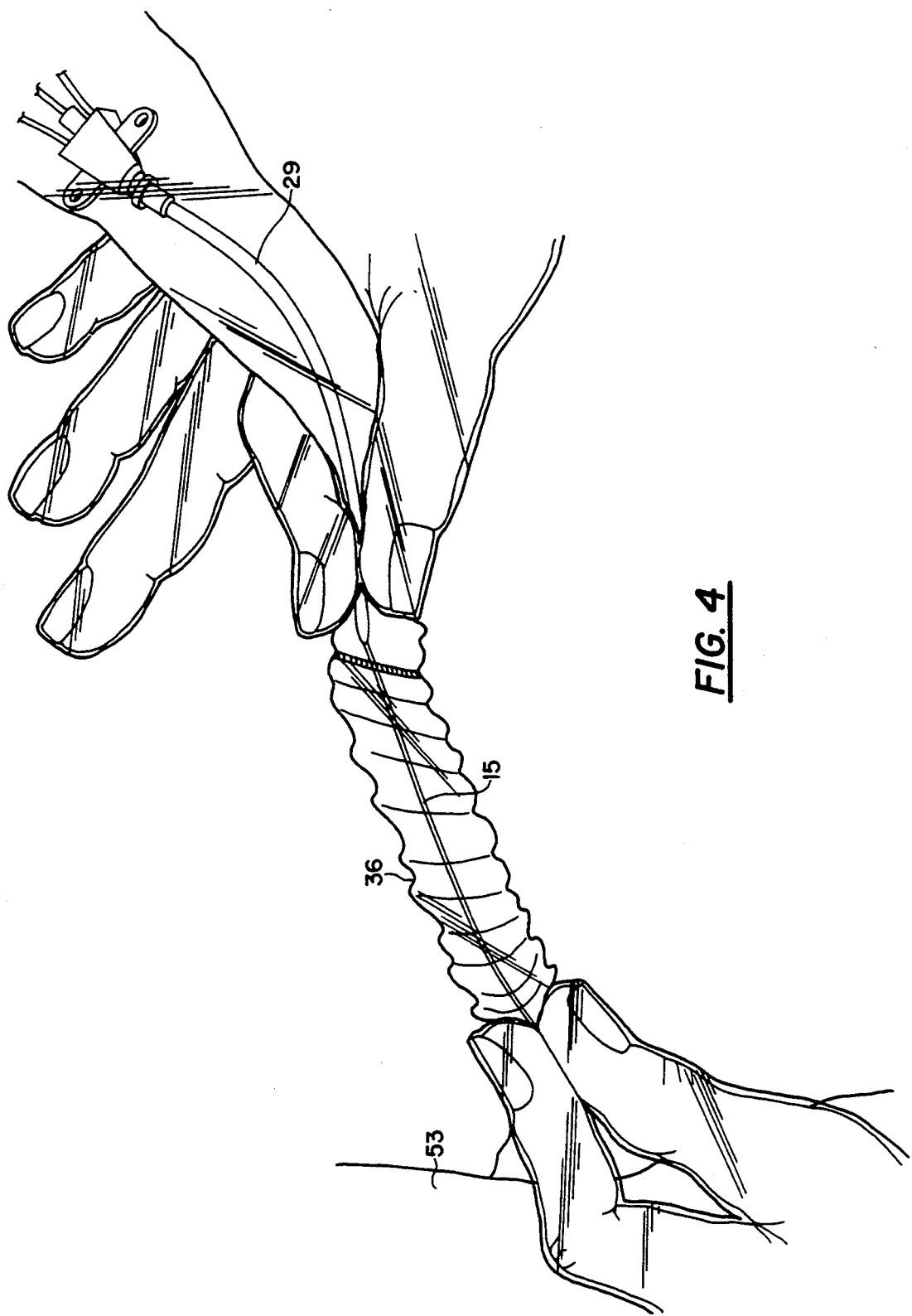
FIG. 4 illustrates the operation of the assembly wherein the physician has grasped the catheter and retracted it from over the guidewire.
Figure 5:
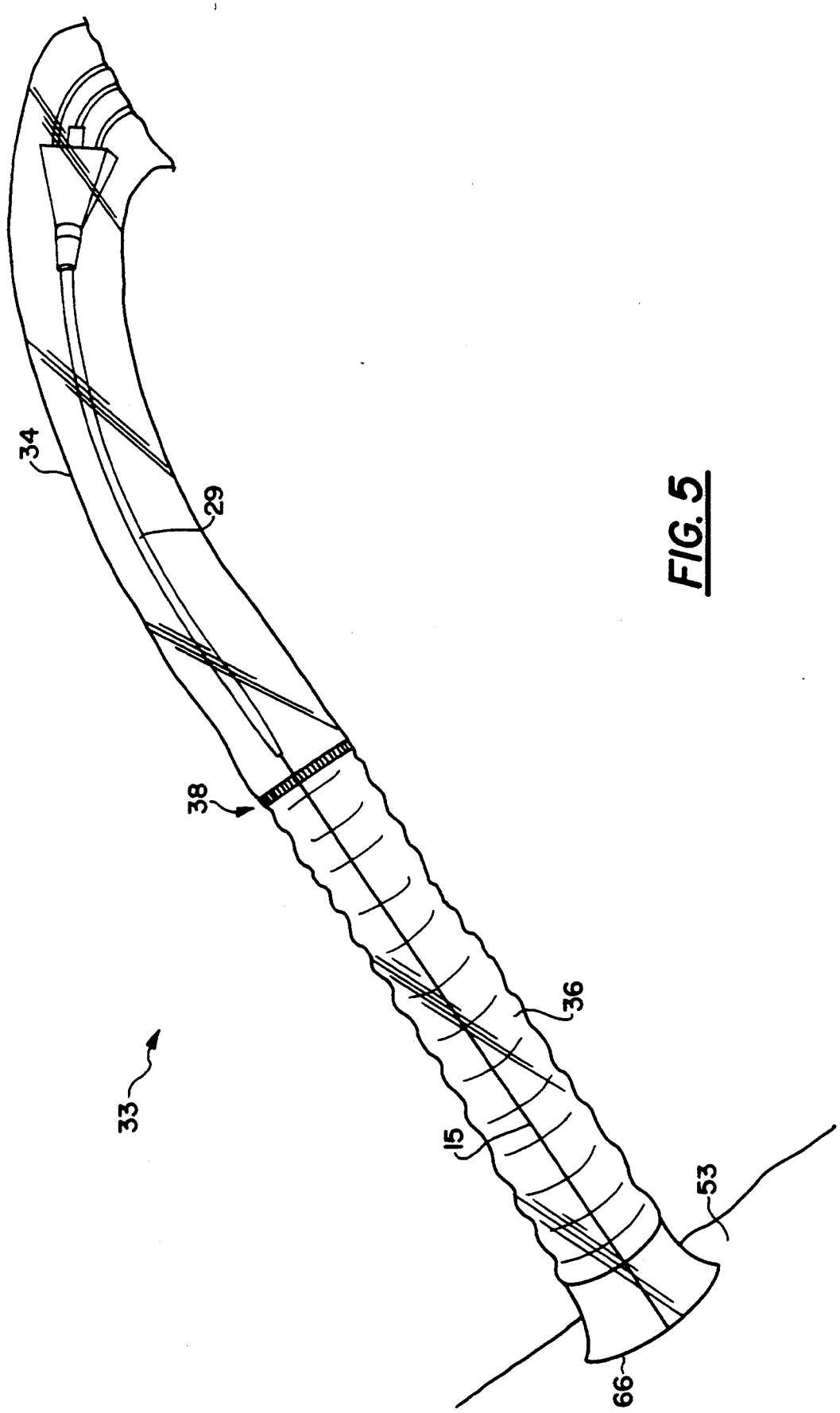
FIG. 5 demonstrates the guidewire barrier in its fully expanded position after the catheter has been completely retracted from over the guidewire.
Figure 6:
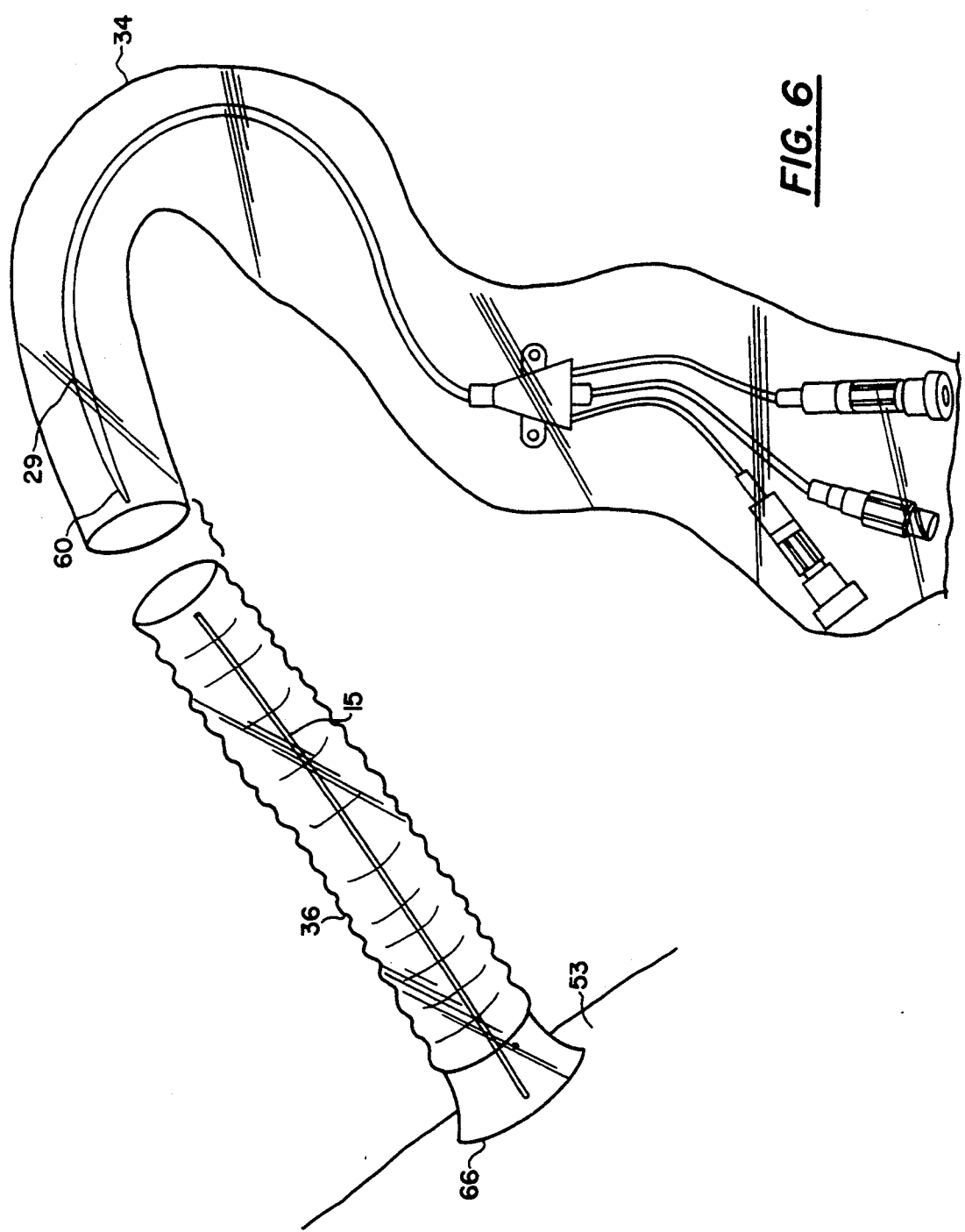
FIG. 6 illustrates separation of the catheter barrier and the guidewire barrier along the weakened portion.
Figure 7:
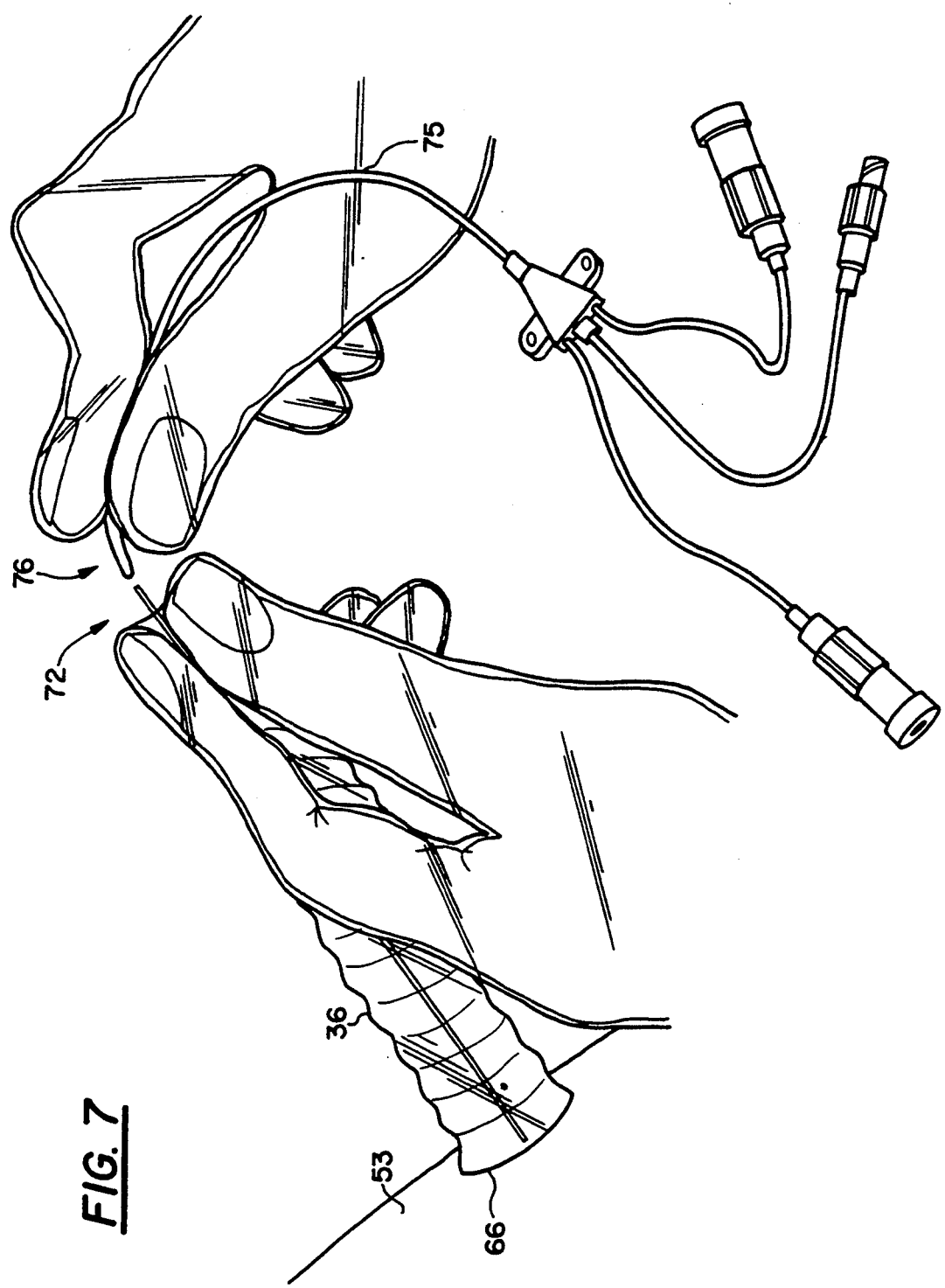
FIG. 7 illustrates placement of a new sterile catheter over the indwelling guidewire.

In operation, the area of the insertion site of the patient's skin 53 around the old indwelling central venous catheter 29 is prepped with an antiseptic solution. The package 45 is then placed near the distal port 27 of the old multilumen catheter 29. The sterile lid from the package 45 is then removed and the physician attaches the female connector 24 of the guidewire container 14 to the luer of the distal port 27 of the pilot tube 28 while leaving the assembly 12 within the package 45. The physician then clips the proximal and middle port tubes (31 and 32) into their respective clips 17 and 18 near the end portion of the guidewire container 14 so that all three pilot tubes are in relative alignment with the guidewire container 14. Alternatively, the three pilot tubes (31,28, and 32) may be clipped together by clip 54 (as shown in FIG. 2). During this time, the physician avoids touching the proximal portion 55 of the assembly 12 which is still resting in the package 45. The physician then puts on sterile gloves and advances the guidewire 15 by grasping the guidewire 15 through the guidewire contact windows 16. The guidewire 15 is advanced until the proximal end 56 of the guidewire 15 reaches a preselected mark 57 on the guidewire container 14. The physician then grasps the proximal portion 55 of the assembly 12 and elevates the assembly 12 out of the package 45 and holds the assembly 12 with its attached catheter 29 in an elevated position. With the other hand, the physician rolls the catheter barrier 34 over the pilot tubes (28, 31, and 32) and the proximal portion of the catheter 29. After a portion of the catheter 29 has been received within the barrier 34, the physician gently withdraws the catheter 29 from the patient while rolling the catheter barrier 34 over the catheter 29 until the catheter 29 is completely removed from the patient and approximately 2.5–3 cm of guidewire 15 is exposed between the distal tip 60 of the catheter 29 and the patient. The remainder of the distal guidewire portion 15 extends beneath the patient's skin 53 into the blood vessel 64 (FIG. 2). At this point, the catheter barrier 34 is fully extended to the distal tip 60 of the catheter 29 and the physician unrolls the attached folded and compressed guidewire barrier 36 from its formerly enclosed position, rolled within catheter barrier 34 (FIG. 1) to a position over the exposed guidewire 15 (FIG. 2). Adhesive may be included on the inner surface of the distal skin contact portion 66 of the guidewire barrier. At this point, the physician grasps the distal portion of the guidewire barrier 36 and holds the guidewire 15 tightly through the distal portion of the barrier 36, leaving the proximal compressed portion of the guidewire barrier 36 free in its compressed form (FIG. 3). The physician then, with the other hand (FIG. 4), pulls the catheter 29 upward and outward until the catheter 29 is completely removed from over the guidewire 15. Since the physician is holding the distal end of the compressed guidewire barrier 36 during this maneuver, the length of the remainder of the guidewire barrier 36 expands from its compressed form to cover the entire length of the guidewire 15. At this point, the guidewire barrier 36 is fully extended (FIG. 5) and the catheter 29 is within the catheter barrier 34 and the guidewire 15 within the guidewire barrier 36. The physician then grasps both barriers 34 and 36 near the weakened portion 38 with both hands and separates the barriers along its weakened portion 38 (FIG. 6). To that end, the weakened portion 38 preferably has a tear region that is facilitate barrier separation. With one hand, the physician then sets aside the catheter barrier 34 containing the catheter 29 so that the tip 60 of the catheter 29 may later be removed for culture. With one hand (FIG. 7), the physician holds the guidewire barrier 36 upward in a stable position and pushes the guidewire barrier 36 downward to expose approximately 1–2 cm of the proximal end 72 of the guidewire 15. With the other hand, the physician reaches into the sterile package 45 and grasps the new prepared catheter 75. The tip 76 of new sterile catheter 75 is then advanced over the guidewire 15 into the guidewire barrier 36 and then into the patient at the insertion site 53. Once the catheter has been advanced the proper distance (generally 8–12 cm) into the patient, the guidewire 15 is removed from the catheter 75 and the new catheter 75 is secured and dressed in the usual fashion. The entire guidewire exchange process can, therefore, be carried out simply, with considerable speed, and without the potential risk of contact contamination of the new catheter. It is clear that many modifications can be made within the scope of the present invention. For example, the catheter and guidewire barrier may initially be separate parts from the guidewire container and assembled at the time of use. Although the cylindrical configuration of the catheter and the guidewire barriers is presently preferred, other configurations are possible. For example, these barriers could be planar, having a perforation for being received over and connecting to the guidewire container and then subsequently unfolded over the catheter and guidewire.

Although the preferred embodiments of this invention has been described, it will be obvious to those skilled in the art that various changes and modifications may be made therein without departing from the invention. Therefore, the claims are intended to include all such changes and modifications may be made therein without departing from the invention. Therefore, the claims are intended to include all such changes and modifications that fall within the true spirit and scope of the invention.

What is claimed:

1. A guidewire insertion assembly for inserting a guidewire into a catheter within a patient, the catheter having fluid terminal, the assembly comprising:
    a) an elongated container having a distal end and a proximal end, said distal end including means for engaging said fluid terminal,
    b) a guidewire contained within said elongated container,
    c) said container further including an interrupted portion along said container proximal to said engaging means, said portion having a length and width sufficient to allow the opposed thumb and finger of a physician to directly contact and grasp said guidewire along said interrupted portion and advance said guidewire from said container into said catheter, and
    d) a barrier system coupled to said container and selectively extendable therefrom for receiving and enclosing said catheter when said catheter is retracted from said patient.

2. The assembly of claim 1 wherein said engaging means comprises a connector.

3. The assembly of claim 2, wherein said connector comprises a female connector for being received over said terminal.

4. The assembly of claim 2, wherein said terminal includes thread means for connecting said connector to said terminal.

5. The assembly of claim 1, wherein said barrier system further includes means for enclosing said guidewire after said guidewire has been received into said catheter and further after said catheter has been removed from over said guidewire and received by said barrier system.

6. The assembly of claim 1, wherein said barrier system includes a first portion for enclosing said catheter and a second portion for enclosing said guidewire.

7. The assembly of claim 6, wherein said second portion is covered by said first portion prior to use.

8. The assembly of claim 6, wherein said first portion is rolled and said second portion is disposed within said rolled first portion prior to use.

9. The assembly of claim 8, wherein said said second portion is folded, said first portion unrolling during use to enclose said retracted catheter and to expose said second portion.

10. The assembly of claim 9 wherein said second portion comprises means to enclose said guidewire when said catheter is removed from over said guidewire.

11. The assembly of claim 6 wherein said second portion includes means to adhere to the skin of the patient adjacent and surrounding said guidewire.

12. The assembly of claim 6 further including a weakened portion and wherein said first portion and said second portion are connected adjacent said weakened portion.

13. The assembly of claim 12 wherein said barrier comprises a flexible plastic housing, said weakened portion includes a tear region and wherein said region has a lesser thickness than said barrier.

14. The assembly of claim 12 wherein said weakened portion comprises a perforated region.

15. The assembly of claim 12 wherein said first portion has a length greater that the length of said catheter.

16. The assembly of claim 15 wherein said weakened portion comprises a weakened area so that when said first and second portions are forcibly retracted from each other, said tear point is disrupted to separate said first portion from said second portion.

17. A method for the sterile exchange of an old catheter having a distal end for a new catheter over a guidewire using a catheter exchange system having a sterile barrier, the method comprising steps of
    a) advancing said guidewire into said catheter,
    b) advancing said barrier over said catheter,
    c) retracting said catheter into said barrier,
    d) retracting said catheter from over said guidewire,
    e) disrupting said barrier near the distal end of said catheter,
    f) advancing said new catheter over said guidewire into said patient.

18. A sterile barrier system for protecting the sterility of a sterile guidewire during the exchange of a new sterile catheter for an old non-sterile catheter having at least one proximal fluid terminal, over said guidewire, the system including an assembly having a distal end for engaging said fluid terminal and said assembly further including a portion proximal to said distal end, the system further comprising:
   a) a flexible tubular barrier having an internal dimension sufficient to receive said proximal terminal of said catheter, said barrier being secured to said assembly proximal to said distal end,
   b) at least a portion of said barrier being folded back upon itself prior to use so that when said barrier is gradually unfolded to be advanced over said catheter, sterile segments of said barrier are sequentially exposed to said catheter, and said folded portion remains sterile until it is unfolded to contact said non-sterile catheter.

19. A rolled sterile barrier system for protecting the sterility of a guidewire during catheter exchange, said barrier system including a tubular sterile barrier having an open distal end and a proximal end and further having a first proximal portion and a second distal portion, said barrier initially being rolled up, with said distal portion being rolled within said proximal portion, and a weakened portion defined intermediate said first and second portions for separating said first and second portions when said barrier is unrolled and said guidewire is enclosed within said second portion of said barrier; and
   further comprising a guidewire container, said tubular barrier being connected to said guidewire container.

20. The system of claim 19 wherein said weakened portion is defined along said barrier at least 20 cm distal to the proximal end of said barrier.

21. The system of claim 19 wherein said unrolled barrier defines an expanded barrier and wherein said expanded barrier defines a cavity extending at least 20 cm beyond said guidewire container to maintain the sterility of said guidewire within said expanded portion.

22. In a guidewire exchange system for exchanging a new sterile catheter for an old catheter, said exchange system including a guidewire container and a flexible guidewire contained within said container, and a tubular sterile barrier assembly disposed in surrounding relation to at least a portion of the length of said container, at least a portion of said barrier assembly being moveable from a first substantially unexpanded position to a second expanded position, said barrier assembly extending beyond said container to define a tubular cavity when said barrier assembly has been moved to said expanded position, said cavity functioning to enclose at least said old catheter therewithin after said guidewire has been advanced into said old catheter and said old catheter has been retracted from over said guidewire into said cavity.

23. A sterile barrier system for protecting from contact contamination a distal end of an old catheter during and after the exchange of said old catheter for a sterile catheter over a guidewire, said old catheter having a proximal connector portion including at least two pigtail terminals, said system comprising:
   a flexible tubular barrier having a first open end and a second end, said barrier further having a length so as to be able to receive substantially the entire length of said old catheter thereinto when said old catheter is retracted from said patient and said barrier is advanced over said old catheter, said barrier being folded back upon itself and being adapted to and sized to receive all of said pigtail terminals of said connector portion of said old catheter, so that when said connector portion of said old catheter is received into said barrier, said barrier is thereafter unfoldable so as to progressively receive the old catheter, whereby said first end of said barrier is free from contact with said connector portion of said old catheter and said first end encloses said distal end of said old catheter when said barrier is fully advanced over said distal end of said old catheter so that upon removal of said distal end of said old catheter from said patient, said distal end is protected from contact contamination with the environment by said first end of said barrier, said system further comprising
   an assembly for aligning said pigtail terminals adjacent one another to facilitate advancing said barrier over said terminals.

24. A method for sterile exchange of an old catheter from within a patient's blood vessel, the old, contaminated multilumen catheter having a distal end and a proximal connector end comprising a plurality of pigtail terminals, for a new sterile multilumen catheter using a catheter exchange system having a tubular sterile barrier and a guidewire, the method comprising steps of:
   a) advancing said guidewire into said old catheter,
   b) advancing said barrier from proximal to said old catheter over said proximal connector end of said old catheter,
   c) retracting said old catheter out of said patient's blood vessel,
   d) further advancing said tubular barrier to enclose said catheter so that said distal end of said catheter is enclosed by said barrier and protected from contact contamination with microorganisms from the ambient environment,
   e) further retracting said old catheter off said guidewire into said barrier;
   f) advancing said new sterile catheter over said guidewire and into said patient's blood vessel.

25. The method of claim 24 further including the step of aligning said pigtail terminals before advancing said barrier thereover.

26. The method of claim 24, wherein said step of further advancing said barrier comprises unrolling said barrier to progressively enclose said old catheter.

27. The method of claim 24, further comprising the step of removing said distal end of said catheter for microbiological evaluation of said distal end.

28. A sterile barrier catheter exchange system for sterile exchange over a guidewire of an old contaminated catheter having a tip within a blood vessel for a sterile catheter, and further for protecting from contact contamination a distal end of said old catheter during and after the exchange of said old catheter, said old catheter having a proximal connector portion including at least two pigtail terminals, said guidewire being of greater length than said catheter, said guidewire including a proximal portion and a distal portion, said proximal portion projecting proximally from said catheter connector portion after said guidewire has been sufficiently advanced through said catheter such that said distal portion projects from said catheter tip into said blood vessel, said system comprising:

a flexible tubular barrier having a first open end and a second end portion, said barrier further having a length so as to be able to receive substantially the entire length of said old catheter thereinto when said old catheter is retracted from said patient and said barrier is advanced over said old catheter, said barrier being folded back upon itself and being adapted to and sized to receive said proximal guidewire portion and all of said pigtail terminals of said connector portion of said old catheter, so that when said proximal guidewire portion and said connector portion of said old catheter is received into said barrier, said barrier is thereafter unfoldable so as to progressively receive the old catheter, whereby said proximal guidewire portion is protected from contact contamination by said when said barrier is being advanced over said catheter and further whereby said first end of said barrier is free from contact contamination with said connector portion of said old catheter and whereby said first end encloses said distal end of said old catheter when said barrier is fully advanced over said distal end of said old catheter so that upon removal of said distal end of said old catheter from said patient, said distal end is protected from contact contamination with the environment by said first end of said barrier.

* * * * *